(12) United States Patent
Kröpke et al.

(10) Patent No.: US 8,779,007 B2
(45) Date of Patent: Jul. 15, 2014

(54) PREPARATION CONTAINING DIOL

(75) Inventors: Rainer Kröpke, Schenefeld (DE); Jens Nielsen, Henstedt-Ulzburg (DE); Kathrin Wolter, Hamburg (DE)

(73) Assignee: Beiersdorf AG, Hamburg (DE)

( * ) Notice: Subject to any disclaimer, the term of this patent is extended or adjusted under 35 U.S.C. 154(b) by 847 days.

(21) Appl. No.: 11/467,404

(22) Filed: Aug. 25, 2006

(65) Prior Publication Data

US 2007/0041916 A1    Feb. 22, 2007

Related U.S. Application Data

(63) Continuation of application No. 10/915,143, filed on Aug. 9, 2004, now abandoned, which is a continuation of application No. PCT/EP03/01204, filed on Feb. 7, 2003.

(30) Foreign Application Priority Data

Feb. 8, 2002    (DE) .................................. 102 05 190

(51) Int. Cl.
*A61K 31/045* (2006.01)
*A61K 8/02* (2006.01)
*A61K 8/00* (2006.01)

(52) U.S. Cl.
USPC .......................................... 514/738; 424/401

(58) Field of Classification Search
USPC ......................................................... 424/401
See application file for complete search history.

(56) References Cited

U.S. PATENT DOCUMENTS

| | | | |
|---|---|---|---|
| 4,242,137 A | 12/1980 | Minuto | |
| 5,716,604 A | 2/1998 | Coe et al. | |
| 5,741,480 A | 4/1998 | Ascione | |
| 5,798,111 A * | 8/1998 | Kanga et al. | 424/401 |
| 5,827,520 A | 10/1998 | de Salvert | |
| 5,977,188 A | 11/1999 | Okamoto et al. | |
| 6,013,248 A | 1/2000 | Luebbe et al. | |
| 6,015,548 A * | 1/2000 | Siddiqui et al. | 424/59 |
| 6,036,964 A | 3/2000 | Guenin et al. | |
| 6,113,888 A | 9/2000 | Castro et al. | |
| 6,214,322 B1 | 4/2001 | Castro et al. | |
| 6,231,837 B1 | 5/2001 | Stroud et al. | |
| 6,403,109 B1 | 6/2002 | Stora | |
| 2001/0051169 A1 | 12/2001 | Saint-Leger | |
| 2002/0146378 A1 | 10/2002 | Rose et al. | |

FOREIGN PATENT DOCUMENTS

| | | |
|---|---|---|
| EP | 0 411 202 B1 | 2/1991 |
| EP | 0 564 277 B1 | 10/1993 |
| EP | 0 636 024 B1 | 2/1995 |
| EP | 0 742 002 B1 | 11/1996 |
| EP | 0 785 714 B1 | 7/1997 |
| EP | 1 283 031 A2 | 2/2003 |
| FR | 2 780 283 | 12/1999 |
| FR | 2 804 320 | 8/2001 |
| WO | 97/14398 A1 | 4/1997 |
| WO | WO 98/58624 | 12/1998 |
| WO | WO 99/44577 | 9/1999 |
| WO | WO 00/56277 | 9/2000 |
| WO | WO 01/95870 | 12/2001 |

OTHER PUBLICATIONS

Sparks, Kathleen et al.; "MP Diol Glycol: a new raw material for personal care"; Drug and Cosmetic Industry; Mar. 1997; pp. 30-32; vol. 160, No. 3.
English language abstract of DE 19816665 A1, Original Publication Date: Oct. 21, 1999. Date Translated: Dec. 20, 2010.

* cited by examiner

*Primary Examiner* — Sreeni Padmanabhan
*Assistant Examiner* — Jody Karol
(74) *Attorney, Agent, or Firm* — Abel Law Group, LLP

(57) ABSTRACT

The invention is a cosmetic or dermatological formulation comprising a) at least one polyol in a concentration of from 0.1 to 20% by weight, based on the total weight of the formulation, and b) at least one diol selected from the group consisting of 2-methyl-1,3-propanediol, pentanediol, and hexanediol, in a concentration of from 0.1 to 25% by weight, based on the total weight of the formulation. The invention also includes formulations further comprising at least one antioxidant, and formulations further comprising at least one UV filter. The invention also includes a method of moisturizing skin comprising applying the formulation to the skin. The invention further includes a method for reducing the tacky sensation, a method for reducing the viscosity, and a method for increasing the stability of a polyol-containing formulation comprising adding a diol selected from the group consisting of 2-methyl-1,3-propanediol, pentanediol, and hexanediol.

25 Claims, No Drawings

PREPARATION CONTAINING DIOL

CROSS-REFERENCE TO RELATED APPLICATIONS

This is a continuation of U.S. Continuation application Ser. No. 10/915,143, filed Aug. 9, 2004 now abandoned which is a continuation application of PCT/EP03/01204, filed Feb. 7, 2003, both of which are incorporated herein by reference in their entirety, and also claims the benefit of German Priority Application No. 102 05 190.9, filed Feb. 8, 2002.

FIELD OF THE INVENTION

The present invention relates to cosmetic or dermatological formulations comprising one or more polyols in a concentration of 0.1 to 20% by weight, one or more diols from the group consisting of 2-methyl-1,3-propanediol, pentanediol, hexanediol in a concentration of 0.1 to 25% by weight, in each case based on the total weight of the formulation, and the use thereof.

BACKGROUND OF THE INVENTION

The skin is the largest organ of humans. Its many functions (for example for regulation of heat and as a sense organ) include the barrier function, which prevents the skin (and therefore in the end the entire organism) from drying out, certainly the most important. At the same time, the skin acts as a protective device against penetration and uptake of substances from the outside. This barrier function is effected through the epidermis, which as the outermost layer forms the actual protective covering against the environment. With about one tenth of the total thickness, at the same time it is the thinnest layer of the skin.

The task of cosmetic skin care is to strengthen or re-establish the natural function of the skin as a barrier against environmental influences (for example dirt, chemicals, microorganisms) and against the loss of endogenous substances (for example water, natural fats, electrolytes).

The aim of skin care is furthermore to compensate for the loss of fats by the skin caused by daily washing. This is important precisely if the natural capacity for regeneration is not sufficient.

A central task of skin care is moisturizing of the skin. The moisture content of the skin has an important influence on its appearance and its state of health: the higher the water loss, the rougher and more friable the skin becomes. Its elasticity and plasticity decrease, and its intactness is no longer guaranteed. To moisturize the skin, moisturizing substances (moisturizers) which assist the water-binding capacity of the horny layer are added to cosmetic and dermatological formulations. Conventional skin moisturizers, which are employed in almost all cosmetic and dermatological formulations, include the polyols, such as glycerol and sorbitol. In addition, other compounds are also employed, such as ethoxylated polyols and hydrolyzed proteins. Components of the natural moisturizing factor of the skin (NMF), for example urea and certain amino acids, are moreover used.

A great disadvantage of the prior art is the adverse sensory properties of cosmetic or dermatological formulations which comprise polyol-containing moisturizing agents. As a rule, these feel tacky and greasy on the skin and make the corresponding products unattractive to the consumer. To suppress these negative properties, expensive silicone oils and lipids, which increase the preparation costs of the cosmetic/dermatological compositions, must be added the formulations.

SUMMARY OF THE INVENTION

It was therefore the object of the present invention to eliminate this disadvantage of the prior art and to develop inexpensive cosmetic or dermatological formulations with significantly improved sensory properties. In particular, the formulations should not feel tacky. The content of silicone oils and other lipids which reduce the tackiness should be reduced.

Cosmetic and dermatological formulations are employed and consumed by consumers worldwide in the most diverse climate zones. Since the development of cosmetics or dermatological agents is quite involved and expensive, attempts are increasingly being made to develop recipes which can be employed globally under the most diverse climate conditions. However, the heat stability of these highly complex metastable mixtures is relatively limited. At low temperatures of below 5° C. their viscosity increases so severely that the formulations can scarcely still be used or processed. The products also tend towards separating out of water and phase separation at low temperatures and with relatively wide variations in temperature, such as may occur, for example, during transportation.

It was therefore a further object of the present invention to develop heat-stable cosmetic and dermatological formulations which, because of their low viscosity, can also still be used and processed at low temperatures.

Surprisingly, these objects are achieved by cosmetic or dermatological formulations comprising
  a) one or more polyols in a concentration of 0.1 to 20% by weight,
  b) one or more diols from the group consisting of 2-methyl-1,3-propanediol,
     pentanediol, hexanediol in a concentration of 0.1 to 25% by weight,
in each case based on the total weight of the formulation.

The formulations according to the invention are distinguished by a high heat stability and low viscosity at low temperatures. Furthermore, they have excellent sensory properties, such as a low feeling of tackiness on the skin.

DETAILED DESCRIPTION OF THE PREFERRED EMBODIMENTS

It is advantageous according to the invention to employ the polyols in a concentration of 0.1 to 20% by weight, and in particular 1 to 15% by weight, based on the total weight of the formulation.

The polyols which are particularly preferred according to the invention are glycerol, propylene glycol and butylene glycol.

It is furthermore advantageous according to the invention to employ the diols in a concentration of 1 to 15% by weight, and in particular 3 to 8% by weight, based on the total weight of the formulation.

In this context, it is advantageous according to the invention if the ratio of polyols to diols in the cosmetic or dermatological formulations according to the invention is from 5:1 to 1:5, in particular 3:1 to 1:3, and very particularly preferably 2:1 to 1:1.

In this context, 2-methyl-1,3-propanediol is employed as a diol which is particularly preferred according to the invention. 2-Methyl-1,3-propanediol [INCI: Methyl Propanediol, for example MPDiol (Lyondell)] is an odorless moisturizing agent having the following structure:

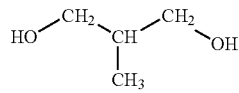

The formulations in the context of the present invention can preferably additionally comprise, in addition to one or more oily phases, one or more aqueous phases and can be, for example, in the form of W/O, O/W, W/O/W or O/W/O emulsions. Such formulations can preferably also be a microemulsion, a solids emulsion (i.e. an emulsion which is stabilized by solids, for example a Pickering emulsion), a sprayable emulsion or a hydrodispersion. Advantageous embodiments of the formulations according to the invention are, for example, ointments, creams and lotions. The formulations in the context of the present invention can furthermore also be anhydrous systems (powders, oils or wax sticks) or oil-free systems (aqueous, aqueous/alcoholic or only alcoholic solutions). The particular corresponding emulsifiers can be employed for this purpose.

The cosmetic or dermatological formulations according to the invention can comprise cosmetic auxiliaries such as are conventionally used in such formulations, for example emulsifiers, preservatives, preservation aids, bactericides, UV light protection filters, perfumes, agents which bleach the skin, self-tanning agents, repellents, substances for preventing foaming, dyestuffs, pigments which have a coloring action or act as UV light protection filters, thickeners, further moisturizing and/or moisture-retaining substances, fillers which improve the sensation on the skin, fats, oils, waxes or other conventional constituents of a cosmetic or dermatological formulation, such as alcohols, polymers, foam stabilizers, electrolytes, organic solvents or silicone derivatives.

The aqueous phase of the formulations according to the invention can advantageously comprise conventional cosmetic auxiliaries, such as, for example, alcohols, in particular those of low C number, preferably ethanol or isopropanol, further diols or polyols of low C number and ethers thereof, preferably ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, dihydroxyacetone and, in particular, one or more thickeners, which can advantageously be chosen from the group consisting of silicon dioxide, aluminum silicates, polysaccharides or derivatives thereof, for example hyaluronic acid, xanthan gum, hydroxypropylmethylcellulose, particularly advantageously from the group consisting of polyacrylates, preferably a polyacrylate from the group consisting of the so-called Carbopols, for example Carbopols of the types 980, 981, 1382, 2984, 5984, in each case individually or in combination.

Copolymers of $C_{10-30}$-alkyl acrylates and one or more monomers of acrylic acid, methacrylic acid or esters thereof are furthermore advantageous.

Compounds which bear the INCI name "Acrylates/$C_{10-30}$ Alkyl Acrylate Crosspolymer" are advantageous. Those obtainable under the trade names Pemulen TR1 and Pemulen TR2 from B. F. Goodrich Company are advantageous in particular.

Compounds which bear the INCI name Ammonium Acryloyldimethyltaurate/Vinylpyrrolidone Copolymer are advantageous.

Advantageously, according to the invention, the ammonium acryloyldimethyltaurate/Vinylpyrrolidone copolymer(s) advantageously have the empirical formula $[C_7H_{16}N_2SO_4]_n$ $[C_6H_9NO]_m$, corresponding to a statistical structure as follows

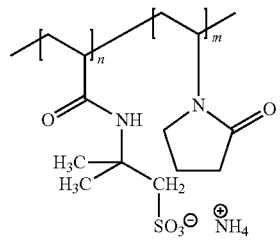

Preferred species in the context of the present invention are filed in the Chemical Abstracts under Registry Numbers 58374-69-9, 13162-05-5 and 88-12-0 and are obtainable under the trade name Aristoflex® AVC from Clariant GmbH.

Copolymers/crosspolymers comprising Acryloyldimethyl Taurate, such as, for example, Simugel® EG or Simugel® EG from Seppic S.A. are furthermore advantageous.

Further thickeners which are advantageously to be used according to the invention are also polyurethanes which are soluble or dispersible in water. Polyurethane-1 or polyurethane-4, for example, are advantageous in the context of the present invention.

Particularly advantageous polyurethanes in the context of the present invention are the types available under the trade name Avalure™ UR from B. F. Goodrich Company, such as, for example, Avalure™ UR 445, Avalure™ UR 450 and the like. The polyurethane obtainable under the trade name Luviset Pur from BASF is furthermore advantageous in the context of the present invention.

The cosmetic or dermatological formulations according to the invention can furthermore advantageously, although not necessarily, comprise fillers, which for example further improve the sensory and cosmetic properties of the formulations and, for example, cause or intensify a velvety or silky sensation on the skin. Advantageous fillers in the context of the present invention are starch and starch derivatives (such as for example tapioca starch, distarch phosphate, aluminum or sodium starch octenyl succinate and the like), pigments which have neither a chiefly UV filter nor a coloring action (such as for example boron nitride etc.) and Aerosils® (CAS no. 7631-86-9).

The oily phase of the cosmetic or dermatological formulations according to the invention is advantageously chosen from the group consisting of polar oils, for example from the group consisting of lecithins and fatty acid triglycerides, namely the triglycerol esters of saturated or unsaturated, branched or unbranched alkanecarboxylic acids of a chain length of 8 to 24, in particular 12 to 18 C atoms.

The fatty acid triglycerides can advantageously be chosen, for example, from the group consisting of synthetic, semi-synthetic and naturally occurring oils, such as for example coco-glyceride, olive oil, sunflower oil, soya oil, groundnut oil, rapeseed oil, almond oil, palm oil, coconut oil, castor oil, wheat germ oil, grape seed oil, thistle oil, evening primrose oil, macadamia nut oil and more of the like.

Naturally occurring waxes of animal and plant origin for example are furthermore advantageous according to the invention, such as, for example, beeswax and other insect waxes and berry wax, shea butter and lanolin (wool wax).

Further advantageous polar oil components can furthermore be chosen in the context of the present invention from the group consisting of esters of saturated or unsaturated, branched or unbranched alkanecarboxylic acids of a chain length of 3 to 30 C atoms and saturated or unsaturated, branched or unbranched alcohols of a chain length of 3 to 30 C atoms and from the group consisting of esters of aromatic carboxylic acids and saturated or unsaturated, branched or unbranched alcohols of a chain length of 3 to 30 C atoms. Such ester oils can then advantageously be chosen from the group consisting of octyl palmitate, octyl cocoate, octyl isostearate, octyl dodeceylmyristate, octyldodecanol, cetearyl isononanoate, isopropyl myristate, iso-propyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semi-synthetic and naturally occurring mixtures of such esters, such as for example jojoba oil.

The oily phase can furthermore advantageously be chosen from the group consisting of dialkyl ethers and dialkyl carbonates, and advantageous compounds are for example dicaprylyl ether (Cetiol OE) and dicaprylyl carbonate, for example that obtainable under the trade name Cetiol CC from Cognis.

It is furthermore preferable to have the oil component(s) from the group consisting of isoeicosane, neopentylglycol diheptanoate, propylene glycol dicaprylate/dicaprate, caprylic/capric/diglyceryl succinate, butylene glycol dicaprylate/dicaprate, coco-glycerides (for example Myritol® 331 from Henkel), $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is particularly advantageous if the oily phase of the formulations according to the invention has a content of $C_{12-15}$-alkyl benzoate, or consists entirely of this.

Advantageous oil components are furthermore for example butyloctyl salicylate (for example that obtainable under the trade name Hallbrite BHB from CP Hall), hexadecyl benzoate and butyloctyl benzoate and mixtures thereof (Hallstar AB) and diethylhexyl naphthalate (Hallbrite TQ from CP Hall or Corapan®TQ from Haarmann & Reimer).

Any desired blends of such oil and wax components are also advantageously to be employed in the context of the present invention.

The oily phase can furthermore likewise advantageously also comprise non-polar oils, for example those which are chosen from the group consisting of branched and unbranched hydrocarbons and hydrocarbon waxes, in particular mineral oil, Vaseline (petrolatum), paraffin oil, squalane and squalene, polyolefins, hydrogenated polyisobutenes and isohexadecane. Among the polyolefins, polydecenes are the preferred substances.

The oily phase can furthermore advantageously have a content of cyclic or linear silicone oils or consist entirely of such oils, although it is preferable to use an additional content of other oily phase components in addition to the silicone oil or the silicone oils.

Silicone oils are high molecular weight synthetic polymeric compounds in which silicon atoms are linked in a chain- or net-like manner via oxygen atoms and the remaining valencies of the silicon are satisfied by hydrocarbon radicals (usually methyl groups, less frequently ethyl, propyl, phenyl groups and the like). The silicone oils are systematically called polyorganosiloxanes. The methyl-substituted polyorganosiloxanes, which represent the most important compounds of this group in terms of amount, are distinguished by the following structural formula

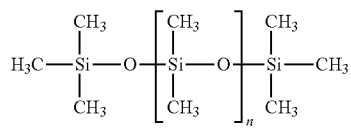

are also called polydimethylsiloxane or dimethicone (INCI). There are dimethicones in various chain lengths and with various molecular weights.

Particularly advantageous polyorganosiloxanes in the context of the present invention are, for example, dimethylpolysiloxanes [poly(dimethylsiloxane)], which are obtainable, for example, under the trade names Abil 10 to 10 000 from Th. Goldschmidt. Phenylmethylpolysiloxanes (INCI: Phenyl Dimethicone, Phenyl Trimethicone) cyclic silicones (octamethylcyclotetrasiloxane or decamethylcyclopentasiloxane), which according to the INCI are also called Cyclomethicone, amino-modified silicones (INCI: Amodimethicone) and silicone waxes, for example polysiloxane/polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are obtainable as various Abil wax types from Th. Goldschmidt, are furthermore advantageous. However, other silicone oils are also advantageously to be used in the context of the present invention, for example cetyldimethicone, hexamethylcyclotrisiloxane, polydimethylsiloxane, poly(methylphenylsiloxane).

Advantageous preservatives in the context of the present invention are, for example, agents which split off formaldehyde (such as for example DMDM hydantoin, which is obtainable, for example, under the trade name Glydant™ from Lonza), iodopropyl butyl carbamates (for example those obtainable under the trade names Glydant-2000, Glycacil-L, Glycacil-S from Lonza or Dekaben LMB from Jan Dekker), parabens (i.e. p-hydroxybenzoic acid alkyl esters, such as methyl, ethyl, propyl or butyl paraben), phenoxyethanol, ethanol, benzoic acid and more of the like. The preservation system furthermore advantageously also conventionally comprises, according to the invention, preservation aids, such as, for example, ethylhexyloxyglycerol, glycine soya etc.

Particularly advantageous formulations are furthermore obtained if antioxidants are employed as additives or active compounds. According to the invention, the formulations advantageously comprise one or more antioxidants. All the antioxidants which are suitable or usual for cosmetic or dermatological uses can be used as antioxidants which are favorable but nevertheless optionally to be used.

Water-soluble antioxidants, such as, for example, vitamins, for example ascorbic acid and derivatives thereof, can be particularly advantageously employed in the context of the present invention.

Preferred antioxidants are furthermore vitamin E and derivatives thereof and vitamin A and derivatives thereof.

The amount of antioxidants (one or more compounds) in the formulations is preferably 0.001 to 30 wt. %, particularly preferably 0.05 to 20 wt. %, in particular 0.1 to 10 wt. %, based on the total weight of the formulation.

If vitamin E and/or derivatives thereof are the antioxidant(s), it is advantageous to choose the particular concentration thereof from the range from 0.001 to 10 wt. %, based on the total weight of the formulation.

If vitamin A or vitamin A derivatives or carotenes or derivatives thereof are the antioxidant(s), it is advantageous to choose the particular concentrations thereof from the range from 0.001 to 10 wt. %, based on the total weight of the formulation.

It is particularly advantageous if the cosmetic or dermatological formulations according to the present invention comprise cosmetic or dermatological active compounds, preferred active compounds being antioxidants which can protect the skin from oxidative stress.

Further advantageous active compounds in the context of the present invention are naturally occurring active compounds and derivatives thereof, such as for example alpha-liponic acid, phytoene, D-biotin, coenzyme Q10, alpha-glucosylrutin, carnitine, carnosine, naturally occurring or synthetic isoflavonoids, creatine, taurine and/or β-alanine.

Recipes according to the invention which for example comprise known antiwrinkling active compounds, such as flavone glycosides (in particular α-glycosylrutin), coenzyme Q10, vitamin E and derivatives and the like, are particularly advantageously suitable for the prophylaxis and treatment of cosmetic or dermatological skin changes, such as occur for example during ageing of the skin (such as, for example, dryness, roughness and development of dryness wrinkles, itching, reduced re-oiling (for example after washing), visible dilations of vessels (telangiectases, cuperosis), flaccidity and the development of folds and wrinkles, local hyper-, hypo- and dyspigmentations (for example senile keratosis), increased susceptibility to mechanical stress (for example chapping) and the like). They are moreover advantageously suitable against the development of dry or rough skin. Cosmetic or dermatological formulations in the context of the present invention can advantageously comprise at least one UV-A, UV-B and/or broad-band filter substance. The formulations may, although not necessarily, optionally also comprise further organic or inorganic pigments as UV filter substances, which can be present in the aqueous and/or the oily phase.

UV filter substances which are liquid at room temperature and are particularly advantageous in the context of the present invention are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 4-methoxycinnamic acid (2-ethylhexyl)ester (2-ethylhexyl 4-methoxycinnamate, INCI: Octyl Methoxycinnamate) and 4-methoxycinnamic acid isopentyl ester (isopentyl 4-methoxycinnamate, INCI: Isoamyl p-Methoxycinnamate).

Advantageous UV-A filter substances in the context of the present invention are dibenzoylmethane derivatives, in particular 4-(tert-butyl)-4'-methoxydiben-zoylmethane (CAS no. 70356-09-1), which is sold by Givaudan under the trademark Parsol® 1789 and by Merck under the trade name Eusolex® 9020.

Advantageous further UV filter substances in the context of the present invention are sulphonated, water-soluble UV filters, such as for example:
  phenylene-1,4-bis-(2-benzimidazyl)-3,3'-5,5'-tetrasulphonic acid and its salts, in particular the corresponding sodium, potassium or triethanolammonium salts, in particular phenylene-1,4-bis-(2-benzimidazyl)-3,3'-5,5'-tetrasulphonic acid bis-sodium salt with the INCI name Bisimidazylate (CAS no.: 180898-37-7), which is obtainable, for example, under the trade name Neo Heliopan AP from Haarmann & Reimer;
  salts of 2-phenylbenzimidazole-5-sulphonic acid, such as its sodium, potassium or its triethanolammonium salt, and the sulphonic acid itself with the INCI name Phenylbenzimidazole Sulphonic Acid (CAS no. 27503-81-7), which is obtainable, for example, under the trade name Eusolex 232 from Merck or under Neo Heliopan Hydro from Haarmann & Reimer;
  1,4-di(2-oxo-10-sulpho-3-bornylidenemethyl)-benzene (also: 3,3'-(1,4-phenylenedimethylene)-bis-(7,7-dimethyl-2-oxo-bicyclo-[2.2.1]hept-1-ylmethanesulphonic acid) and salts thereof (especially the corresponding 10-sulphato compounds, in particular the corresponding sodium, potassium or triethanolammonium salt), which is also called benzene-1,4-di(2-oxo-3-bornyli-denemethyl-10-sulphonic acid). Benzene-1,4-di(2-oxo-3-bornylidenemethyl-10-sulphonic acid has the INCI name Terephthalidene Dicamphor Sulphonic Acid (CAS no.: 90457-82-2) and is obtainable, for example, under the trade name Mexoryl SX from Chimex;
  sulphonic acid derivatives of 3-benzylidenecamphor, such as for example 4-(2-oxo-3-bornylidenemethyl)benzenesulphonic acid, 2-methyl-5-(2-oxo-3-bornyli-denemethyl)sulphonic acid and salts thereof.

Advantageous UV filter substances in the context of the present invention are furthermore so-called broad-band filters, i.e. filter substances which absorb both UV-A and UV-B radiation.

Advantageous broad-band filters or UV-B filter substances are, for example, triazine derivatives, such as for example
  2,4-bis-{[4-(2-ethyl-hexyloxy)-2-hydroxy]-phenyl}-6-(4-methoxyphenyl)-1,3,5-triazine (INCI: Aniso Triazine), which is obtainable under the trade name Tinosorb® S from CIBA-Chemikalien GmbH;
  diethylhexylbutylamidotriazone (INCI: Diethylhexylbuta-midotriazone), which is obtainable under the trade name UVASORB HEB from Sigma 3V;
  4,4',4"-(1,3,5-triazine-2,4,6-triyltriimino)-tris-benzoic acid tris(2-ethylhexyl ester), also: 2,4,6-tris-[anilino-(p-carbo-2'-ethyl-1'-hexyloxy)]-1,3,5-triazine (INCI: ethylhexyl triazone), which is marketed by BASF Aktiengesellschaft under the trade name UVINUL® T 150.

The further UV filter substances can be oil-soluble or water-soluble.

Advantageous oil-soluble UV-B and/or broad-band filter substances in the context of the present invention are for example:
  3-benzylidenecamphor derivatives, preferably 3-(4-methylbenzylidene)camphor, 3-benzylidenecamphor;
  4-aminobenzoic acid derivatives, preferably 4-(dimethylamino)-benzoic acid (2-ethylhexyl)ester, 4-(dimethylamino)benzoic acid amyl ester;
  derivatives of benzophenone, preferably 2-hydroxy-4-methoxybenzophenone, 2-hydroxy-4-methoxy-4'-methylbenzophenone, 2,2'-dihydroxy-4-methoxybenzophe-none
  and UV filters bonded to polymers.
  (3-(4-(2,2-bis ethoxycarbonylvinyl)-phenoxy)propenyl)-methoxysilane/dimethylsiloxane—copolymer which is obtainable, for example, under the trade name Parsol® SLX from Hoffmann La Roche.

Further light protection filter substances which are advantageously to be used according to the invention are ethylhexyl 2-cyano-3,3-diphenylacrylate(octocrylene), which is obtainable from BASF under the name Uvinul® N 539, and hydroxybenzophenones, such as 2-(4'-(diethylamino)-2'-hydroxybenzoyl)-benzoic acid hexyl ester.

Particularly advantageous formulations in the context of the present invention which are distinguished by a high or very high UV-A and/or UV-B protection preferably furthermore comprise, in addition to the filter substance(s) according to the invention, further UV-A and/or broad-band filters, in particular dibenzoylmethane derivatives [for example 4-(tert-butyl)-4'-methoxydibenzoylmethane], phenylene-1,4-bis-(2-benzimidazyl)-3,3'-5,5'-tetrasulphonic acid and/or its salts, 1,4-di(2-oxo-10-sulpho-3-bornylidenemethyl)-benzene and/or salts thereof and/or 2,4-bis-{[4-(2-ethylhexyloxy)-2-hydroxy]-phenyl}-6-(4-methoxyphenyl)-1,3,5-triazine, in each case individually or in any desired combinations with one another.

The list of UV filters mentioned which can be employed in the context of the present invention is of course not intended to be limiting.

The formulations according to the invention advantageously comprise the substances which absorb UV radiation in the UV-A and/or UV-B range in a total amount of for example 0.1 wt. % to 30 wt. %, preferably 0.5 to 20 wt. %, in particular 1.0 to 15.0 wt. %, in each case based on the total weight of the formulations, in order to provide cosmetic formulations which protect the hair or the skin from the entire range of ultraviolet radiation.

Preferred further inorganic pigments are metal oxides or other metal compounds which are sparingly soluble or insoluble in water, in particular oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$), cerium (for example $Ce_2O_3$), mixed oxides of the corresponding metals and blends of such oxides as well as barium sulphate ($BaSO_4$).

In the context of the present invention, the pigments can advantageously also be used in the form of commercially obtainable oily or aqueous predispersions. Dispersing auxiliaries and/or solubilization mediators can advantageously be added to these predispersions.

According to the invention, the pigments can advantageously be treated on the surface ("coated"), whereby, for example, a hydrophilic, amphiphilic or hydrophobic character is to be formed or retained. This surface treatment can comprise providing the pigments with a thin hydrophilic or hydrophobic inorganic or organic layer by processes known per se. The various surface coatings can also comprise water in the context of the present invention.

It may furthermore be of advantage, where appropriate, to incorporate film-forming agents into the formulations according to the invention, for example in order to improve the water-resistance of the formulations or to increase the UV protection performance (UV-A and/or UV-B boosting). Both water-soluble or dispersible and fat-soluble film-forming agents, in each case individually or in combination with one another, are suitable.

Advantageous water-soluble or dispersible film-forming agents are for example polyurethanes (for example the Avalure® types from Goodrich), Dimethicone Copolyol Polyacrylate (Silsoft Surface® from Witco Organo Silicones Group), PVP/VA (VA=vinyl acetate) copolymer (Luviscol VA 64 Powder from BASF) etc.

Advantageous fat-soluble film-forming agents are for example the film-forming agents from the group consisting of polymers based on polyvinylpyrrolidone (PVP)

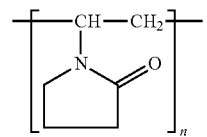

Copolymers of polyvinylpyrrolidone, for example PVP Hexadecene Copolymer and PVP Eicosene Copolymer, which are obtainable under the trade names Antaron V216 and Antaron V220 from GAF Chemicals Cooperation, and Tricontayl PVP and more of the like are particularly preferred.

According to their make-up, cosmetic or topical dermatological compositions in the context of the present invention can be used, for example, as skin protection cream, cleansing milk, make-up remover, day or night cream etc. It may be possible and advantageous to use the compositions according to the invention as a base for pharmaceutical formulations. Generally, the invention relates to the use of formulations according to the invention as an ointment, cream, milk, lotion or spray for protecting the skin and/or skin appendages and/or against UV radiation.

The invention furthermore relates to the use of diols for improving the sensory properties, in particular for reducing the tacky sensation on the skin, of polyol-containing cosmetic or dermatological formulations, the use of diols for reducing the viscosity of cosmetic or dermatological formulations at temperatures below 10° C. and the use of diols for increasing the stability of cosmetic or dermatological formulations The invention also relates to the use of 2-methyl-1,3-propanediol as a moisturizing agent.

The following examples are intended to illustrate the present invention without limiting it. Unless stated otherwise, all the amounts data, contents and percentage contents are based on the weight and the total amount or on the total weight of the formulations.

| W/O Emulsions | | | | | |
|---|---|---|---|---|---|
| | 1 | 2 | 3 | 4 | 5 |
| Triglycerol diisostearate | 1.0 | 0.5 | 0.25 | 2.0 | 3.0 |
| Diglycerol dipolyhydroxystearate | 1.0 | 1.5 | 1.75 | 3.0 | 2.0 |
| Paraffin oil | 12.5 | 10.0 | 8.0 | 5.0 | 7.5 |
| Vaseline | 1.0 | — | 1.5 | — | — |
| Hydrogenated coconut glycerides | 0.5 | 0.1 | 1.5 | — | 0.25 |
| Decyl oleate | 0.5 | 0.75 | 1.0 | 2.0 | 0.25 |
| Octyldodecanol | 0.5 | 1.0 | 0.75 | 3.0 | 0.25 |
| Aluminum stearate | 0.04 | — | — | 0.2 | 0.05 |
| Dicaprylyl carbonate | 0.1 | 0.05 | 0.15 | 0.5 | 1.0 |
| Magnesium sulphate | 0.5 | 0.6 | 0.5 | 0.7 | 1.0 |
| Glycerol | — | 5.0 | — | 15.0 | 5 |
| Propylene glycol | 5.0 | — | 10.0 | — | — |
| Butylene glycol | — | — | — | — | 5.0 |

-continued

| | | | | | |
|---|---|---|---|---|---|
| 2-Methyl-1,3-propanediol | 5.0 | 2.5 | 10.0 | 8.5 | 1.0 |
| Citric acid | 0.2 | 0.1 | 0.2 | 0.3 | 1.0 |
| Perfume | q.s. | q.s. | q.s. | q.s. | q.s. |
| Ethanol | 2.0 | — | 5.0 | — | 10.0 |
| Caprylic/capric acid triglyceride | 2.0 | 2.5 | 3.0 | 5.0 | 0.5 |
| Methyl paraben | 0.4 | 0.15 | 0.05 | 0.3 | 0.4 |
| Propyl paraben | 0.3 | 0.4 | 0.25 | 0.15 | — |
| Iodopropynyl butyl carbamate | — | — | 0.05 | — | 0.1 |
| Water | to 100 | to 100 | to 100 | to 100 | to 100 |

| | 6 | 7 | 8 | 9 | 10 |
|---|---|---|---|---|---|
| PEG-30 Dipolyhydroxystearate | — | 0.5 | 0.25 | — | 3.0 |
| Lanolin Alcohol | 1.0 | 1.5 | 1.75 | 3.0 | — |
| Paraffin oil | 12.5 | 10.0 | 8.0 | 5.0 | 17.5 |
| Vaseline | 8.0 | 6.0 | 5.0 | 2.0 | 2.5 |
| 2-Methyl-1,3-propanediol | 5.0 | 2.5 | 15.0 | 7.5 | 10.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Aluminum stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Magnesium sulphate | 0.5 | 0.6 | 0.5 | 0.7 | 1.0 |
| Glycerol | 3.0 | 5.0 | — | — | 2.0 |
| Propylene glycol | 5.0 | — | 10.0 | — | — |
| Butylene glycol | — | — | — | 3.0 | 5.0 |
| Citric acid | 0.2 | 0.1 | 0.2 | 0.3 | 1.0 |
| Perfume | q.s. | q.s. | q.s. | q.s. | q.s. |
| 1,3-Butylene glycol | 2.0 | — | 5.0 | — | — |
| Caprylic/capric acid triglyceride | 2.0 | 2.5 | 3.0 | 5.0 | 0.5 |
| Methyl paraben | 0.4 | 0.15 | 0.05 | 0.3 | 0.4 |
| Propyl paraben | 0.3 | 0.4 | 0.25 | 0.15 | — |
| Water | to 100 | to 100 | to 100 | to 100 | to 100 |

| | 11 | 12 | 13 | 14 | 15 |
|---|---|---|---|---|---|
| Cetyl dimethicone copolyol | 1.0 | — | — | 3.0 | 5.0 |
| Cylomethicone + PEG/PPG-18/18 Dimethicone | 10.0 | 12.5 | 25 | — | — |
| Cyclomethicone | 12.5 | 15 | 8 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Panthenol | 0.5 | 1.0 | 0.75 | 0.25 | 0.1 |
| Sodium chloride | 2.0 | 0.6 | 2.5 | 0.7 | 1.0 |
| Glycerol | 3.0 | — | 2.0 | 3.0 | 15 |
| Propylene glycol | 5.0 | 5.0 | 5.0 | — | — |
| Butylene glycol | — | — | 4.0 | — | 2.0 |
| 2-Methyl-1,3-propanediol | 15.0 | 2.5 | 10.0 | 8.5 | 1.0 |
| Citric acid | 0.2 | 0.1 | 0.2 | 0.3 | 1.0 |
| Perfume | q.s. | q.s. | q.s. | q.s. | q.s. |
| Methyl paraben | 0.4 | 0.1 | 0.05 | 0.3 | 0.4 |
| Propyl paraben | 0.3 | 0.4 | 0.25 | 0.15 | — |
| Cetyldimethicone | 0.5 | — | 0.7 | — | — |
| Iodopropynyl butyl carbamate | — | — | 0.05 | — | 0.1 |
| Modified starch | — | 2.5 | — | 0.15 | — |
| Water | to 100 | to 100 | to 100 | to 100 | to 100 |

| | 16 | 17 | 18 | 19 | 20 |
|---|---|---|---|---|---|
| Cetyl dimethicone copolyol | 1.0 | — | — | 3.0 | 5.0 |
| Cylomethicone + PEG/PPG-18/18 Dimethicone | 10.0 | 12.5 | 25 | — | — |
| Cyclomethicone | 12.5 | 15 | 28.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Panthenol | 0.5 | 1.0 | 0.75 | 0.25 | 0.1 |
| 2-Methyl-1,3-propanediol | 5.0 | 2.5 | 10.0 | 8.5 | 1.0 |
| Glycerol | 3.0 | — | 2.0 | 3.0 | 15 |
| Propylene glycol | 5.0 | 5.0 | 5.0 | — | — |
| Butylene glycol | — | — | 4.0 | — | 2.0 |
| Sodium chloride | 2.0 | 0.6 | 2.5 | 0.7 | 1.0 |
| Sorbitol | 3.0 | 5.0 | 10.0 | 15.0 | 1.5 |
| Citric acid | 0.2 | 0.1 | 0.2 | 0.3 | 1.0 |
| Perfume | q.s. | q.s. | q.s. | q.s. | q.s. |
| Methyl paraben | 0.4 | 0.1 | 0.05 | 0.3 | 0.4 |
| Propyl paraben | 0.3 | 0.4 | 0.25 | 0.15 | — |
| Stearyldimethicone | 0.5 | — | 0.7 | — | — |

-continued

|  |  |  | 0.05 |  | 0.1 |
|---|---|---|---|---|---|
| Iodopropynyl butyl carbamate | — | — | 0.05 | — | 0.1 |
| Modified starch | — | 2.5 | — | 0.15 | — |
| Water | to 100 | to 100 | to 100 | to 100 | to 100 |

Oil-in-Water Emulsions

|  | 21 | 22 | 23 | 24 | 25 |
|---|---|---|---|---|---|
| Glyceryl sterate | 1.0 | — | — | 3.0 | 5.0 |
| PEG-40 stearate | 10.0 | — | 5 | — | — |
| Triglycerol methylglucose distearate | — | 5.5 | — | — | 2.5 |
| Sorbitan stearate | — | 1.5 | 3 | — | — |
| Cyclomethicone | 1 | 2.5 | 5 | 7.5 | 3 |
| Dimethicone | 5.0 | 13.0 | 5.0 | 12.0 | 15.0 |
| Behenyl alcohol | 0.1 | — | 0.2 | 0.5 | — |
| Stearyl alcohol | — | 1 | — | 1 | — |
| Cetylstearyl alcohol | — | — | 0.1 | 1 | — |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| 2-Methyl-1,3-propanediol | 5.0 | 2.5 | 10.0 | 8.5 | 1.0 |
| Panthenol | 0.5 | 1.0 | 0.75 | 0.25 | 0.1 |
| Glycerol | 3.0 | — | 2.0 | 3.0 | 15 |
| Propylene glycol | 5.0 | 5.0 | 5.0 | — | — |
| Butylene glycol | — | — | 4.0 | — | 2.0 |
| Perfume | q.s. | q.s. | q.s. | q.s. | q.s. |
| Methyl paraben | 0.4 | 0.1 | 0.05 | 0.3 | 0.4 |
| Propyl paraben | 0.3 | 0.4 | 0.25 | 0.15 | — |
| Iodopropynyl butyl carbamate | — | — | 0.05 | — | 0.1 |
| Modified starch | — | 2.5 | — | 0.15 | — |
| Water | to 100 | to 100 | to 100 | to 100 | to 100 |

|  | 26 | 27 | 28 | 29 | 30 |
|---|---|---|---|---|---|
| Polyethylene glycol (21) stearyl ether | 1 | — | 2.5 | 2 | 1.5 |
| Polyethylene glycol (2) stearyl ether | 1 | — | 1.5 | 3 | 1.5 |
| Cetearyl glucoside | — | 8 | — | — | — |
| Cyclomethicone | 2.5 | 3 | 12.5 | 2 | 8.0 |
| Dimethicone | 5.0 | 13.0 | 5.0 | 12.0 | 5.0 |
| Behenyl alcohol | 0.3 | 0.5 | — | 0.1 | — |
| Stearyl alcohol | 0.3 | — | — | 0.2 | — |
| Cetylstearyl alcohol | 0.3 | 0.5 | — | — | 0.25 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| 2-Methyl-1,3-propanediol | 15.0 | 2.5 | 10.0 | 8.5 | 25.0 |
| Panthenol | 0.5 | 1.0 | 0.75 | 0.25 | 0.1 |
| Glycerol | 3.0 | — | 2.0 | 3.0 | 15 |
| Propylene glycol | 5.0 | 5.0 | 5.0 | — | — |
| Butylene glycol | — | — | 4.0 | — | 2.0 |
| Perfume | q.s. | q.s. | q.s. | q.s. | q.s. |
| Methyl paraben | 0.4 | 0.1 | 0.05 | 0.3 | 0.4 |
| Propyl paraben | 0.3 | 0.4 | 0.25 | 0.15 | — |
| Iodopropynyl butyl carbamate | — | — | 0.05 | — | 0.1 |
| Modified starch | — | 2.5 | — | 0.15 | — |
| Water | to 100 | to 100 | to 100 | to 100 | to 100 |

That which is claimed:

1. A cosmetic or dermatological formulation, wherein the formulation is present as an ointment, a cream, a milk, a lotion or a spray and comprises
    (a) one or more of glycerol, propylene glycol, and butylene glycol in a total concentration of from 0.1% to 20% by weight, based on a total weight of the formulation,
    (b) 2-methyl-1,3-propanediol and, one or both of pentanediol and hexanediol in a total concentration of from 1% to 25% by weight, based on the total weight of the formulation, 2-methyl-1,3-propanediol being present in a concentration of from 1% to 15% by weight, and
    (c) at least one substance selected from antioxidants, alpha-lipoic acid, phytoene, D-biotin, coenzyme Q10, α-glucosylrutin, carnitine, carnosine, isoflavonoids, creatine, taurine, and β-alanine,
and wherein a ratio of (a) to (b) is from 5:1 to 1:1.

2. The formulation of claim 1, wherein glycerol, propylene glycol, butylene glycol and 2-methyl-1,3-propanediol are present in a total concentration of at least 7.5% by weight.

3. The formulation of claim 1, wherein (a) comprises glycerol.

4. The formulation of claim 1, wherein (b) comprises pentanediol.

5. The formulation of claim 1, wherein (b) comprises hexanediol.

6. The formulation of claim 1, wherein (c) comprises at least one antioxidant.

7. The formulation of claim 6, wherein the at least one antioxidant comprises at least one of vitamin A and carotene.

8. The formulation of claim 1, wherein (c) comprises at least one substance selected from alpha-lipoic acid, phytoene, D-biotin, coenzyme Q10, α-glucosylrutin, carnitine, carnosine, isoflavonoids, creatine, taurine, and β-alanine.

9. The formulation of claim 1, wherein the formulation comprises at least one UV filter.

10. The formulation of claim 1, wherein (b) is present in a total concentration of from 3% to 8% by weight.

11. The formulation of claim 1, wherein (a) is present in a total concentration of from 1% to 15% by weight.

12. The formulation of claim 11, wherein the ratio of (a) to (b) is from 2:1 to 1:1.

13. The formulation of claim 1, wherein (a) comprises at least one of propylene glycol and butylene glycol.

14. A cosmetic or dermatological formulation, wherein the formulation is present as an ointment, a cream, a milk, a lotion or a spray and comprises
   (a) one or both of propylene glycol and butylene glycol and, optionally, glycerol in a total concentration of from 0.1% to 20% by weight, based on a total weight of the formulation, and
   (b) 2-methyl-1,3-propanediol and, one or both of pentanediol and hexanediol in a total concentration of from 1 to 25% by weight, based on the total weight of the formulation, 2-methyl-1,3-propanediol being present in a concentration of from 1% to 15% by weight,
and wherein a ratio of (a) to (b) is from 1:3 to 3:1.

15. The formulation of claim 14, wherein glycerol, propylene glycol, butylene glycol and 2-methyl-1,3-propanediol are present in a total concentration of at least 7.5% by weight.

16. The formulation of claim 14, wherein (b) comprises.

17. The formulation of claim 14, wherein (b) is present in a total concentration of from 3% to 8% by weight.

18. The formulation of claim 14, wherein the ratio of (a) to (b) is from 2:1 to 1:1.

19. A cosmetic or dermatological formulation, wherein the formulation is present as an ointment, a cream, a milk, a lotion or a spray and comprises
   (a) one or more of glycerol, propylene glycol, and butylene glycol in a total concentration of from 0.1% to 20% by weight, based on a total weight of the formulation, and
   (b) 2-methyl-1,3-propanediol and one or both of pentanediol and hexanediol in a total concentration of from 1% to 25% by weight, based on the total weight of the formulation, 2-methyl-1,3-propanediol being present in a concentration of from 1% to 15% by weight,
and wherein a ratio of (a) to (b) is from 1:3 to 3:1.

20. The formulation of claim 19, wherein (b) is present in a total concentration of from 3% to 8% by weight.

21. The formulation of claim 19, wherein the ratio of (a) to (b) is from 2:1 to 1:1.

22. A cosmetic or dermatological formulation, wherein the formulation is present as an ointment, a cream, a milk, a lotion or a spray and comprises
   (a) one or more of glycerol, propylene glycol, and butylene glycol in a total concentration of from 1% to 15% by weight, based on a total weight of the formulation,
   (b) 2-methyl-1,3-propanediol and, one or both of pentanediol and hexanediol in a total concentration of from 1% to 25% by weight, based on the total weight of the formulation, 2-methyl-1,3-propanediol being present in a concentration of from 1% to 8% by weight, and
   (c) at least one substance selected from antioxidants, alpha-lipoic acid, phytoene, D-biotin, coenzyme Q10, α-glucosylrutin, carnitine, carnosine, isoflavonoids, creatine, taurine, and β-alanine,
and wherein a ratio of (a) to (b) is from 3:1 to 1:1.

23. The formulation of claim 22, wherein (b) is present in a total concentration of from 3% to 8% by weight.

24. A cosmetic or dermatological formulation, wherein the formulation is present as an ointment, a cream, a milk, a lotion or a spray and comprises
   (a) one or more of glycerol, propylene glycol and butylene glycol in a total concentration of from 1% to 15% by weight, based on a total weight of the formulation,
   (b) 2-methyl-1,3-propanediol and, one or both of pentanediol and hexanediol in a total concentration of from 3% to 8% by weight, based on the total weight of the formulation, 2-methyl-1,3-propanediol being present in a concentration of from 3% to 8% by weight, and
   (c) at least one substance selected from vitamin A, carotene, alpha-lipoic acid, phytoene, coenzyme Q10, α-glucosylrutin, carnitine, carnosine, isoflavonoids, creatine, taurine, and β-alanine,
and wherein a ratio of (a) to (b) is from 2:1 to 1:1.

25. A cosmetic or dermatological formulation, wherein the formulation is present as an ointment, a cream, a milk, a lotion or a spray and comprises
   (a) at least two of glycerol, propylene glycol and butylene glycol in a total concentration of from 1% to 15% by weight, based on a total weight of the formulation,
   (b) 2-methyl-1,3-propanediol and, one or both of pentanediol and hexanediol in a total concentration of from 3% to 8% by weight, based on the total weight of the formulation, 2-methyl-1,3-propanediol being present in a concentration of from 1% to 8% by weight, and
   (c) at least one substance selected from alpha-lipoic acid, phytoene, coenzyme Q10, α-glucosylrutin, carnitine, carnosine, isoflavonoids, creatine, taurine, and β-alanine,
and wherein a ratio of (a) to (b) is from 5:1 to 1:1.

* * * * *